United States Patent [19]

Kanno

[11] 4,411,866
[45] Oct. 25, 1983

[54] STEAM STERILIZATION METHOD FOR ARTIFICIAL ORGAN ASSEMBLIES AND RESULTANT STERILIZED PRODUCT

[75] Inventor: Michio Kanno, Higashikurume, Japan

[73] Assignee: Terumo Corporation, Tokyo, Japan

[21] Appl. No.: 335,862

[22] Filed: Dec. 30, 1981

Related U.S. Application Data

[63] Continuation of Ser. No. 133,815, Mar. 25, 1980, abandoned.

[30] Foreign Application Priority Data

Mar. 28, 1979 [JP] Japan ................... 54-36728

[51] Int. Cl.³ .................. A61L 2/06; B65D 81/20
[52] U.S. Cl. ........................ 422/25; 206/204;
206/205; 206/210; 210/321.3; 210/321.4; 422/26
[58] Field of Search ........... 210/321 R, 321 B, 321 A, 210/321; 422/25, 26, 27, 9, 38; 206/204, 205, 210

[56] References Cited

U.S. PATENT DOCUMENTS 2,812,231 1/1957 Zar ................... 206/204 X
3,342,328 9/1967 Swenson .............. 210/321
3,506,126 4/1970 Serfass et al. ......... 210/96.2
3,880,759 4/1975 Van Assendelft .......... 210/194
3,964,479 6/1976 Boag et al. ............. 210/90
4,176,156 11/1979 Asanuma et al. ......... 422/25

FOREIGN PATENT DOCUMENTS 2722474 11/1978 Fed. Rep. of Germany ........ 422/38
2369846 6/1978 France .
2383668 10/1978 France .
53-101890 5/1978 Japan .
1264833 2/1972 United Kingdom .
1555605 11/1979 United Kingdom .

Primary Examiner—Barry S. Richman
Attorney, Agent, or Firm—Frishauf, Holtz, Goodman and Woodward

[57] ABSTRACT

An artificial organ assembly having an artificial organ with a built-in body fluid treatment mechanism as well as a body fluid inlet port and a body fluid outlet port, filled with a liquid harmless to the human body and sealed. It also includes an extracorporeal body fluid circulation mechanism comprising a body fluid inlet line connected to the body fluid inlet port and a body fluid outlet line connected to the body fluid outlet port, filled with a liquid harmless to the human body and sealed. The whole assembly is hermetically vacuum-packaged and steam sterilized in the packaged state.

2 Claims, 3 Drawing Figures

STEAM STERILIZATION METHOD FOR ARTIFICIAL ORGAN ASSEMBLIES AND RESULTANT STERILIZED PRODUCT

This is a continuation of application Ser. No. 133,815, filed Mar. 25, 1980, now abandoned.

BACKGROUND OF THE INVENTION

This invention relates to artificial organ assemblies which are suitable for heat-sterilization with, for example, an autoclave and which eliminate the need for treatments after sterilization, and the sterilization method thereof.

Artificial organ assemblies include, for example, a blood dialysis apparatus which interposes a semipermeable membrane between the blood and a dialysate to extract waste materials and excessive water from the blood into the dialysate. This apparatus is generally called an artificial kidney. Today, blood dialysis apparatus are classified according to their structural characteristics into the coil type, plate type and hollow (tubular) fiber type. Among these, the hollow fiber type blood dialysis apparatus has been widely used due to its more efficient dialysis and the smaller amount of filling liquid required, as well as other advantageous characteristics.

However, the blood dialysis apparatus of the hollow fiber type has about 10,000 fibers of regenerated cellulose for example, bundled together and having an internal diameter between about 200 and 300µ. The blood flows inside each fiber and the dialysate flows outside the fibers, so that there are many problems in sterilization. In other words, in dry sterilization, such as gamma rays or gas sterilization with ethylene oxide, liquid passage is very irregular because the hollow fibers constitute extremely thin capillaries, keeping bubbles therein, and much labor is needed to eliminate bubbles inside the fibers. If the blood dialysis apparatus is first filled with a liquid and offered as a package, labor can be saved and the performance of the hollow fibers can be maintained constant. As an example of such an approach, a wet sterilization method is known wherein liquid sterilizer such as formalin is filled into the apparatus. In the case of formalin sterilization, however, there is a fear that a residue of the sterilizer may remain in the blood dialysis apparatus. To avoid this, a method has been proposed wherein such chemicals as mentioned above are not used, but a physiological saline solution is filled into the artificial organ as described above, and sterilization is carried out in an autoclave under pressure and heat. In this case, there is a fear that cracking or breakdown of the artificial organ may occur with heat expansion of the filled physiological saline solution or other causes, which poses a problem. As a solution to this problem, a method has been proposed wherein a buffer sack attached with a cannula is passed through either the blood port or the dialysate port of the artificial organ, and sterilization is carried out in this state; then the buffer sack is removed and the artificial organ is packed, followed by sterilization with ethylene oxide gas. Alternatively, a method has been proposed wherein a deformable baggy cap is provided as a stopper for either the blood port or the dialysate port of the artificial organ; after sterilization in an autoclave, the baggy cap is removed and replaced with a conventional rubber stopper, followed by packing in an aseptic environment. In these methods are, however, the process between the autoclave sterilization and the achievement of a sterilized package is cumbersome and requires much labor, and the fear of recontamination remains during the treatment following the autoclave sterilization. In other words, in the former method using a buffer sack with a cannula, contamination by mold or germs is possible at the site where the cannula pierces, and in the former method using a baggy stopper, the difficulties of replacing the baggy stopper with a normal cap and of packaging in a perfectly aseptic environment pose problems. Moreover, because these conventional methods involve cooling with water after the autoclave sterilization prior to packing, contamination at this stage must also be considered.

This invention was made in consideration of the situation stated above, and aims to offer artificial organ assemblies that are suitable for sterilization under pressure and heat by such means as an autoclave, to eliminate the need for treatment after sterilization and to require only simple preparation, and a method for sterilization of the assemblies.

Further, this invention aims to provide artificial organ assembly packages that permit rapid heat-sterilization, and further allow a required humidity to be maintained after sterilization.

SUMMARY OF THE INVENTION

This invention provides artificial organ assemblies having an artificial organ with a built-in blood treatment mechanism including a body fluid inlet port and a body fluid outlet port, and being filled with a liquid harmless to the human body and sealed; an external body fluid circulation mechanism including a body fluid inlet line connected to said body fluid inlet port and a body fluid outlet line connected to said body fluid outlet port, said circulation mechanism being filled with a liquid harmless to the human body and sealed; and a package accommodating and enclosing said artificial organ and external body fluid circulation mechanism wherein, upon heat-sterilization, at least a part of the expansion of said liquid harmless to the human body is absorbed by said external body fluid circulation mechanism, whereby heat-sterilization can be carried out in the packaged state. Furthermore, in the heat-sterilization method of artificial organs having a built-in body fluid treatment mechanism, a body fluid inlet port and a body fluid outlet port, this invention provides a sterilization method for artificial organs characterized by connecting an external body fluid circuit to said ports, filling said artificial organ and external body fluid circuit with a liquid harmless to the human body and sealing it, and the whole being heat-sterilized in the sealed state, at least a part of the expansion of said liquid harmless to the human body during said heat-sterilization being absorbed by said external body fluid circulation mechanism.

DETAILED DESCRIPTION

It should be noted that the definition of "a liquid harmless to the human body" as specified in this specification should not be construed in a limited sense, but includes any liquid which is substantially harmless in view of the object of this invention. Accordingly, a liquid harmless to the human body includes, pure water, an aqueous solution of inorganic salts such as sodium chloride, potassium chloride, calcium chloride, magnesium chloride, sodium bicarbonate, and sodium phosphate, an aqueous solution of inorganic acids such as hydrochloric acid and phosphoric acid, an aqueous solution of organic acids such as acetic acid, lactic acid, amino acid and citric acid, an aqueous solution of organic acid salts such as sodium acetate, sodium lactate and sodium citrate, alcohols such as glycerine, an aqueous solutions of sugars such as glucose, mannitol, sorbitol, xylitol and fructose, and an aqueous solution of other electrolytes in the body liquid.

Figure 1:
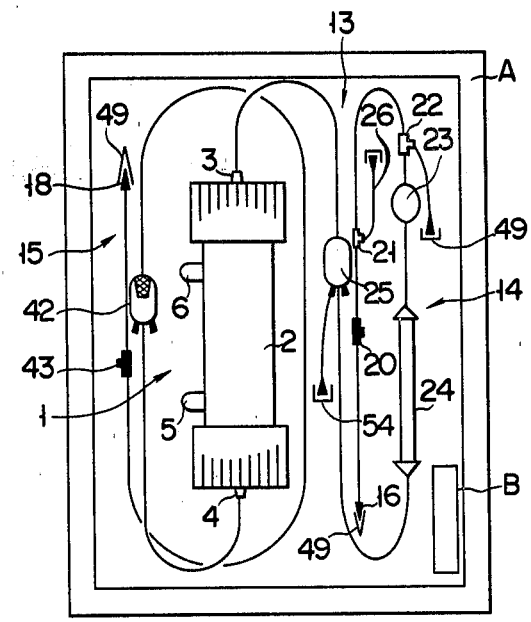
FIG. 1 is a plan view illustrating the packaged state of a hollow fiber type blood dialysis apparatus assembly related to one example of the present invention.
Figure 2:
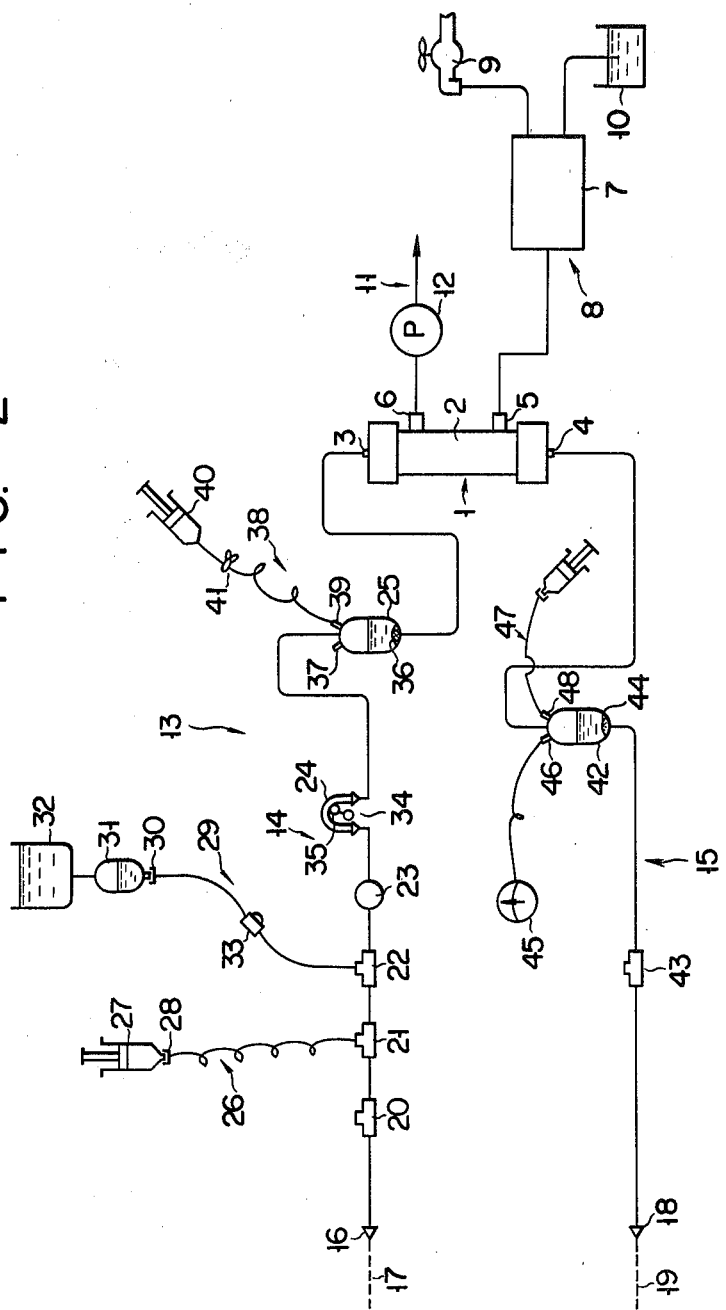
FIG. 2 illustrates the unfolded state of the assembly of FIG. 1.

Referring to FIGS. 1 and 2 showing an example of the present invention, a blood dialysis apparatus will be described, using numerical designations. FIG. 1 illustrates the state of the whole blood dialysis apparatus accommodated in a packaging case A, and the blood dialysis apparatus is to be unfolded upon actual application, as shown in FIG. 2. In the drawings, 1 is a common hollow fiber type blood dialysis apparatus which contains, inside the apparatus body 2, a bundle of hollow fibers, consisting of about 10,000 fibers of regenerated cellulose, or cellulose ester fibers, for example, having an internal diameter between about 200 and 300$\mu$, and simultaneously forming blood paths inside said hollow fibers. Dialysate passes outside the fibers. At one end of the blood path is formed a blood inlet chamber, which is connected to an inlet terminal 3. At the other end of the blood path is formed a blood outlet chamber, which is connected to an outlet terminal 4.

Both ends of said dialysate path are connected respectively to an inlet terminal 5 and an outlet terminal 6, and to said inlet terminal 5 is detachably connected a dialysate feed line 8 equipped with a dialysate source 7 as illustrated in FIG. 2. Either one of terminals 5 or 6 may be omitted in the case of a filtration type artificial organ. In this case filtrate will be drawn out of the organ instead of dialysate. A water tap (or ion exchange equipment, reverse osmosis equipment, or other pure water producing equipment) 9 and a concentrated dialysate tank 10 are connected in parallel to said dialysate source 7 to provide a dialysate, for example, the concentrated solution being diluted 35 times in volume. To the outlet terminal 6, an efflux line 11 is to be detachably connected, and a pump 12 is included in this efflux line 11. The dialysate feed line 8 and the efflux line 11 are attached during actual use.

On the other hand, to the inlet terminal 3 on the blood path side is connected a blood inlet line 14 of an extracorporeal blood circulation mechanism 13, and to the outlet terminal 4 is connected a blood outlet line 15 of the extracorporeal blood circulation mechanism 13. The other end of said blood inlet line 14 has a connector 16 for connecting to the blood inlet terminal 17 of a needle to remain in the patient. At the other end of said blood outlet line 15, a connector 18 is attached, permitting connection to the blood outlet terminal 19 of the needle.

In order to prevent leaking of the filling liquid, a heat-resistive clamping means such as a spring clamp or plastic band should preferably be attached on the connections between inlet and outlet terminals 3, 4 and blood inlet and outlet lines 14, 15 and between connectors 16, 18 and caps 49.

In said blood inlet line 14 are incorporated in series from the inlet side, an injection or sampling site 20, a connector 21 for a heparin line connection, a priming line connector 22, a negative pressure monitor 23, a pump tube 24 for a blood pump 34, and a drip chamber 25, all of which are integrally built into the blood inlet line 14. Said injection or sampling site 20 is provided with a septum through which various drugs may be injected or blood samples for tests may be sampled using a penetrating needle. The connector 21 is provided with a heparin line 26, at the top of which is attached a connector 28 for detachably connecting a heparin injector 27. This is to provide heparin, an anticoagulant, according to the dialysis situation, by mounting and connecting the heparin injector 27 to the connector 28 during dialysis. This heparin line 26 is not always necessary, and can be omitted, for example, when injecting heparin intermittently at fixed intervals without the use of the automatic heparin injector, thus simplifying the blood inlet line.

The priming line connector 22 is connected to a priming line 29, and to the top of this priming line 29 is attached a connector 30. The connector 30 can be connected to a physiological saline solution bag 32 via a drip chamber 31. A clamp 33 is incorporated within the priming line 29 to permit adjustment or shutdown of the physiological saline solution feed. The priming line 29 is used not only for the priming operation in preparation for the start of dialysis, but also for blood transfusions or liquid transfusion operations in the course of dialysis, or further, for blood returning operations at the end of dialysis.

The negative pressure monitor 23 comprises, for example, a hollow spherical elastic body and indicates an abnormality by its deformation when the negative pressure in the arterial-side line 14 becomes extreme. Such an abnormality may be caused, for example, by the tip of an intravascular needle clinging to a blood vessel wall. Therefore, the danger of penetration of the blood vessel wall by the needle tip can be avoided with such a device.

The pump tube 24 for the blood pump comprises a flexible tube and is mounted on a rolling part 35 of the blood pump 34 during operation. In other words, by squeezing said pump tube 24 with the rolling part 35 of the blood pump 34, blood is made to flow.

The drip chamber 25 is for removing bubbles and is provided at the bottom with a filtration net 36. At the top of the drip chamber 25 are located a connection nozzle 37 for a pressure monitor and another connection nozzle 39 for a liquid level adjustment line 38. Said connecting nozzles 37 and 39 are detachably connected, respectively, with a pressure monitor and a liquid level adjustment line. Further, the liquid level adjustment line 38 is provided with a suction bleeder 40 at the top, permitting adjustment of the liquid level by sucking out the gas in the drip chamber 25 as required. To the liquid level adjustment line is clamped a foreceps 1 during use. Similarly, in the blood outlet line 15 of the extracorporeal blood circulation mechanism are incorporated in series from the blood dialysis apparatus, a drip chamber 42, and an injection or sampling site 43. Said drip chamber 42 has the same structure as the aforementioned drip chamber 25 of the blood inlet line 14, and is provided with a filtration net 44 on the bottom, a connecting nozzle for a pressure monitor 45, and another connecting nozzle for a liquid level adjustment line 47 at the top. Said injection sampling site 43 has the same structure as the one in the blood inlet line 15, but from this injection sample site 43 heparin neutralizer, for example, protamine sulfate, is injected.

The blood dialysis apparatus 1 is completed by connecting the blood inlet line 14 with the blood outlet line 15 of the extracorporeal blood circulation mechanism 13. Further, before use, all the ports are sealed which later open to the exterior. Examples of these ports are: the inlet terminal 5 and outlet terminal 6 of the dialysis apparatus, the connector 16 of the blood inlet line 14, the connector 18 of the blood outlet line 15, the connector 28 of the heparin line 26, the connector 30 of the priming line 29, the connecting nozzles 37 and 39 of the blood inlet line drip chamber 25, and the connecting nozzles 46 and 48 of the blood outlet line drip chamber 42. These are provided with water-tight sealing members such as caps 49 . . . , but instead the sealing can be achieved by mutual connection of, for example, connectors 16 and 18 without the caps 49 . . . . In other words, the inside of the blood dialysis apparatus 1 and the extracorporeal blood circulation mechanism 13 are connected sealed from the exterior. The sealed inside is filled with a liquid filling material harmless to the human body, such as physiological saline solution or distilled water. When filling, the inside is evacuated, and filled completely with the liquid filling material. Using such a vacuum method, extremely minute empty pockets, such as the inside of the hollow fibers can be filled without difficulty. In other words, not only the inside of the external blood circulation mechanism 13, but also the blood paths and the dialysate paths which are normally difficult to fill, can be filled efficiently.

Next, an explanation of the sterilizing method for said hollow fiber type blood dialysis apparatus assembly is given. First, after filling the assembly with a liquid filling material as stated above, the open ports are sealed to prevent the liquid from leaking. Then the assembly is put into a packaging case A, preferably by vacuum packing, and the whole package is placed in steam of high temperature and high pressure inside an autoclave for sterilization. Normally the inside of the autoclave is kept at a temperature in the range from 100° to 130° C. with a steam pressure from 1 to 3 kg/cm$^2$, the pressure and temperature being adjustable within these ranges. During sterilization within these temperature and pressure ranges according to known operational methods, the increase in volume of filling liquid due to the temperature increase can be absorbed by expansion of an expandable member, for example a tubular member, of the extracorporeal blood circulation mechanism, so that installation of a baggy buffer device at the liquid port of the blood dialysis apparatus 1, as in conventional methods, is not necessary. In this invention, such expandable materials as rubber can be used as the caps for the liquid inlet and outlet terminals 5, 6 of the artificial organ as illustrated; said volume increase will be distributed to and absorbed by the tubular member etc. of the extracorporeal blood circulation mechanism 13, and there is no danger that the sealing of the packaging case A will be damaged upon heat-sterilization in this case.

Incidentally, a tube having a length of 8 cm or less may be used as the extracorporeal body fluid circulation mechanism.

Figure 3:
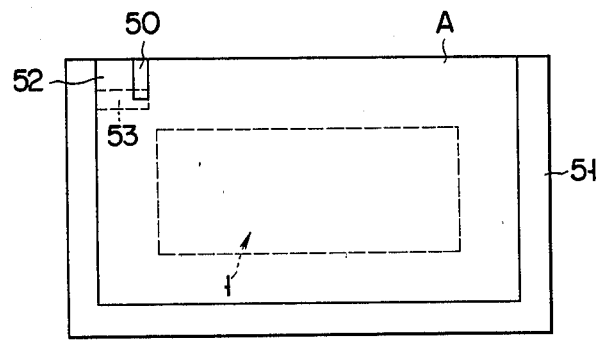
FIG. 3 is a plan view of a package related to another example of the present invention.

The sealing members such as caps 49 . . . must be adequately strong under the temperature and pressure conditions inside the autoclave. Accordingly, those caps made of such synthetic resins as polycarbonate, polypropylene, silicone rubber or synthetic or natural heat-resistive rubber are preferable. Need to say, each part of the blood dialysis apparatus 1 and the extracorporeal blood circulation mechanism 13 must also be made of materials having sufficient heat and water resistance for the high pressure steam sterilization and therefore common polyvinyl chloride, silicone resin, polyurethane, polybutadiene, or similar materials are satisfactory for these units. Except for the tubular members, the material of each member ought to have preferably as little tendency to deform as possible, so that polypropylene or polycarbonate can be used instead of the above-mentioned materials. It is required as a material of the case A to select a material tha does not develop pinholes or break down under high temperature and high humidity and that can maintain a sealed aseptic state. For example, a material that is permeable to steam but is not permeable to germs, or is virtually impermeable to both steam and germs, is used. When using a packaging case of the latter steam-impermeable material, it is preferable to fill in the packaging case enough water to maintain, inside of the packaging case, a pressure higher than the saturation steam pressure at the sterilization temperature. For example, as shown in FIG. 1, this water can be provided by putting in the packaging case an absorbent material B such as filter paper moistened with an appropriate amount of water as the steam source, and packing it with the blood dialysis apparatus etc; or as shown in FIG. 3, by sectioning a corner of the packaging case A to provide a heat-sealed part 50 which provides a water storage section 52 between the peripheral sealing part 51 and the heat-sealed part 50. In the case of the example illustrated in FIG. 3, water scattered after the sterilization can be recollected in the water storage section 52 by means of a centrifuge or other suitable means, and then the opening 53 can be sealed, and if necessary the water storage section 52 can be cut off.

Thus, according to the above example, the assembly is formed by connecting the extracorporeal blood circulation mechanism 13 to the blood dialysis apparatus 1, each part of these is filled with a liquid material harmless to the human body, and the whole is preliminarily sterilized in an environment of high pressure steam. Therefore, without manual labor for connecting the units 1 and 13 and for degassing prior to use, the washing operation (liquid substitution) can be started immediately. This saves labor for the dialysis staff and also permits comparatively unskilled operator's handling or operation in a limited time, and provides an effective means for preventing accidents in limited care units and in home dialysis.

Because the whole device is filled with a liquid material and sterilized with high pressure steam, dissolved materials and impurities contained in the extracorporeal blood circulation mechanism 13 and in the blood dialysis apparatus 1 are extracted into the liquid material and removed simultaneously in the washing operation. Adhesives used for assembling the circuits can also be removed simultaneously.

Further, because the inside of the blood dialysis apparatus is filled with a liquid material such as physiological saline solution, the dialytic membrane is well moistened with the liquid, permitting improved material permeability, ultrafiltration performance, improved affinity to blood, and complete elimination of air bubbles, and allowing a reduction in residual blood.

Because the whole apparatus is unified and packed in a single package, the packaging cost and sterilization overhead costs are lower, resulting in a cost reduction on one hand, and on the other hand, stock control in such facilities as hospitals becomes simpler, and storage space is reduced.

The method of the present invention is free from the drawback inherent in the widely used conventional ethylene oxide gas sterilization method, namely that ethylene oxide permeates into the material of each apparatus member, allegedly triggering such symptoms as eosinophilia. The method of the present invention is also free from the drawback seen in the conventional formalin sterilization method, namely that for avoiding inclusion of bubbles in the blood dialysis apparatus, the blood circuit is preliminarily filled with washing liquid and is connected to the blood dialysis apparatus while the washing liquid overflows from the connecting terminal of the blood circuit; after completing the connection, the formalin in the blood dialysis apparatus is washed out with a large amount of the washing liquid during a long-lasting priming washing which is cumbersome and time-consuming, and which also leaves open the danger of operation errors, such as contamination during the connection between the blood dialysis apparatus and the blood circuit.

It is obvious that application of this invention is not limited to artificial kidney apparatus as shown in the above examples, but is also applicable to artificial lungs, artificial livers and various other artificial organs that involve treatment by passage of body fluids, such as blood, part of blood or abdominal ascites. It is also possible to apply this invention to a body fluid treatment mechanism, which is provided with a filtrate circuit mechanism.

What is claimed is:

1. A steam sterilization method for an artificial organ assembly which includes an artificial organ having a built-in body fluid treatment mechanism which has a body fluid inlet port and a body fluid outlet port, comprising:
   connecting a body fluid inlet line of an extracorporeal body fluid circulation mechanism to said body fluid inlet port;
   connecting a body fluid outlet line of said extracorporeal body fluid circulation mechanism to said body fluid outlet port;
   said extracorporeal body fluid circulation mechanism including a drip chamber and a pump tube coupled between said inlet and outlet lines;
   filling said artificial organ and said extracorporeal body fluid circulation mechanism with a liquid harmless to the human body, and sealing said artificial organ and extracorporeal body fluid circulation mechanism;
   at least one of said artificial organ and said extracorporeal body fluid circulation mechanism having an expandable member;
   hermetically accommodating, enclosing and vacuum-packing said artificial organ and extracorporeal body fluid circulation mechanism in a sealed steam permeable package in a vacuum-packed state without water disposed between said package and said organ and extracorporeal body fluid circulation mechanism;
   said package, artificial organ and extracorporeal body fluid circulation mechanism comprising said artificial organ assembly; and
   steam sterilizing said artificial organ assembly in the sealed vacuum-packaged state at a temperature ranging from 100° to 130° C. and under a pressure ranging from 1 to 3 kg/cm$^2$ of pressure (gauge pressure), wherein any expansion of said harmless liquid during the steam-sterilization is absorbed by said expandable member and any gas generated by the steam-sterilization can be trapped in said drip chamber of said extracorporeal body fluid circulation mechanism.

2. A sterilized artificial organ assembly comprising:
   (i) an artificial organ including a built-in body fluid treatment mechanism having a body fluid inlet port and a body fluid outlet port, said body fluid treatment mechanism being filled with a liquid harmless to the human body and sealed;
   (ii) an extracorporeal body fluid circulation mechanism including a body fluid inlet line connected to said body fluid inlet port, a body fluid outlet line connected to said body fluid outlet port, a drip chamber and a pump tube, said body fluid circulation mechanism being filled with a liquid harmless to the human body and sealed; and
   at least one of said artificial organ and said extracorporeal body fluid circulation mechanism having an expandable member;
   (iii) a steam permeable package hermetically accommodating and enclosing said artificial organ and extracorporeal body fluid circulation mechanism in a vacuum-packaged state without water dispposed between said package and said organ and extracorporeal body fluid circulation mechanism;
   the whole artificial organ assembly being steam-sterilized in the vacuum-packaged state, at a temperature ranging from 100° to 130° C. and under a pressure ranging from 1 to 3 kg/cm$^2$ (gauge pressure), wherein any expansion of said harmless liquid during the steam-sterilization is absorbed by said expandable member and any gas generated by the steam-sterilization can be trapped in said drip chamber by said extracorporeal body fluid circulation mechanism.

* * * * *